United States Patent [19]

Baader et al.

[11] Patent Number: 5,260,323

[45] Date of Patent: Nov. 9, 1993

[54] 2,4- AND 2,5-SUBSTITUTED PYRIDINE-N-OXIDES, PROCESSES FOR THEIR PREPARATION AND THEIR USE

[75] Inventors: Ekkehard Baader, Königstein/Taunus; Martin Bickel, Bad Homburg; Volkmar Günzler-Pukall, Marburg, all of Fed. Rep. of Germany

[73] Assignee: Hoechst Aktiengesellschaft, Frankfurt am Main, Fed. Rep. of Germany

[21] Appl. No.: 978,467

[22] Filed: Nov. 19, 1992

Related U.S. Application Data

[63] Continuation of Ser. No. 721,681, Jun. 26, 1991, abandoned.

Foreign Application Priority Data

Jun. 28, 1990 [DE] Fed. Rep. of Germany ....... 4020570

[51] Int. Cl.⁵ .................. A61K 31/44; A61K 31/455; C07D 211/72; C07D 211/84
[52] U.S. Cl. .................. 514/356; 514/332; 514/333; 514/334; 514/354; 514/355; 514/318; 546/256; 546/257; 546/262; 546/263; 546/316; 546/318; 546/321; 546/322; 546/323; 546/326; 546/193; 546/194
[58] Field of Search ............... 514/354, 355, 356, 333, 514/334, 332, 318; 546/316, 318, 321, 322, 323, 326, 256, 257, 262, 263, 193, 194

[56] References Cited

FOREIGN PATENT DOCUMENTS 0278452 8/1988 European Pat. Off. .
0278453 8/1988 European Pat. Off. .

OTHER PUBLICATIONS

Chemical Abstracts, vol. 67, (1967), No. 21, Nov. 20, 1967, No. 98869w, Columbus, Ohio US; Milos Chvapil et al.: "Mechanisms of the anti-fibrous effect of poly-(-vinyl-pyridine-N-oxide)": & Prac. Lek. 19(5), 206-11 (1967).
Chemical Abstracts, vol. 97, (1982) No. 25, Dec. 20, 1982, No. 215892f, Columbus, Ohio U.S.; & JP 82109792 (Banyu Pharmaceutical Co. Ltd.) Aug. 7, 1982.
B. Brycki et al., "Kinetics and mechanism of acid hydrolysis of 2-carboethozypyridine N-oxides", *Journal of Physical Organic Chemistry*, vol. 3, 489-92 (1990).
Kawata et al. Chem. Abstracts, vol. 105, No. 6, 52229n (1986).
Misic-Vukovic et al. Chem. Abstracts, vol. 92, No. 13; 110323q (1980).
Matsumoto et al., Chem. Abstracts, vol. 80, No. 19; 108385v (1974).

*Primary Examiner*—Johann Richter
*Attorney, Agent, or Firm*—Finnegan, Henderson, Farabow, Garrett & Dunner

[57] ABSTRACT

2,4- and 2,5-substituted pyridine-N-oxides are provided which are effective as fibrosuppressives and immunosuppressives. Said compounds are also suitable for the treatment of disorders of the metabolism of collagen and collagen-like substances or the biosynthesis of C1q.

11 Claims, No Drawings

2,4- AND 2,5-SUBSTITUTED PYRIDINE-N-OXIDES, PROCESSES FOR THEIR PREPARATION AND THEIR USE

This application is a continuation of application Ser. No. 07/721,681 filed Jun. 26, 1991, now abandoned.

Compounds which inhibit the enzymes proline hydroxylase and lysine hydroxylase cause a very selective inhibition of collagen biosynthesis by influencing collagen-specific hydroxylation reactions. In the course thereof, protein-bound proline or lysine is hydroxylated by the enzymes proline hydroxylase or lysine hydroxylase. If this reaction is suppressed by inhibitors, a non-functional, underhydroxylated collagen molecule is formed, which can be released into the extracellular space by the cells only to a small extent. In addition, the underhydroxylated collagen cannot be incorporated into the collagen matrix and is very easily degraded by proteolysis. As a result of these effects, the amount of collagen stored extracellularly is on the whole reduced.

Inhibitors of prolyl hydroxylase are therefore suitable substances in the treatment of disorders in which the storage of collagens contributes decisively to the symptoms. These include, inter alia, fibroses of the lungs, liver and skin (scleroderma) and atherosclerosis.

It is known that the inhibition of proline hydroxylase by known inhibitors such as $\alpha,\alpha'$-dipyridyl leads to an inhibition of $Cl_q$ biosynthesis by macrophages (W. Müller et al., FEBS Lett. 90 (1978), 218; Immunbiology 155 (1978), 47). As a result, a failure of the classical route of complement activation occurs. Inhibitors of proline hydroxylase therefore also act as immunosuppressives, for example in immune complex diseases. It is known that the enzyme proline hydroxylase is effectively inhibited by pyridine-2,4- and -2,5-dicarboxylic acid (K. Majamaa et al., Eur. J. Biochem. 138 (1984) 239–245). However, these compounds are effective in cell culture as inhibitors only in very high concentrations (Tschank, G. et al., Biochem. J. 238 (1987) 625–633).

DE-A 3,432,094 describes pyridine-2,4- and -2,5-dicarboxylic acid diesters having 1-6 carbon atoms in the ester alkyl moiety as pharmaceuticals for the inhibition of proline hydroxylase and lysine hydroxylase.

However, these lower-alkylated diesters have the disadvantage that they are cleaved to the acids too rapidly in the organism and do not reach their site of action in the cell in sufficiently high concentration and are therefore less suitable for possible administration as pharmaceuticals.

DE-A 3,703,959, DE-A 3,703,962 and DE-A 3,703,963 describe in general form mixed ester/amides, higher alkylated diesters and diamides of pyridine-2,4- and -2,5-dicarboxylic acid, which effectively inhibit, collagen biosynthesis in the animal model. Thus, DE-A 3,703,959, inter alia, describes the synthesis of N,N'-bis(2-methoxyethyl)pyridine-2,4-dicarboxamide and N,N'-bis(3-isopropoxypropyl)pyridine-2,4-dicarboxamide.

An improved process for the preparation of N,N'-bis(2-methoxyethyl)pyridine-2,4-dicarboxamide is proposed in German Patent Applications P 38 26 471.4 and P 38 28 140.6.

German Patent Application P 39 24 093.2 proposes novel N,N'-bis(alkoxyalkyl)pyridine-2,4-dicarboxamides.

German Patent Application P 40 01 002.3 describes the use of N,N'-(nitroxyalkyl)pyridine-2,4- and -2,5-dicarboxamides for the preparation of pharmaceuticals inhibiting proline hydroxylase and lysine hydroxylase. Both pyridine-2,4- and -2,5-dicarboxamide (Hirakata et al., J. pharm. Soc. Japan 77 (1957) 219 and Häring et al., Helv. 37 (1954) 147, 153) and pyridine-2,4- and -2,5-dicarboxylic acid dihydrazide (Itai et al., Bl. nation. hyg. Labor. Tokyo, 74 (1956) 115, 117 and Shinohara et al., Chem. High Polymers Japan, 15 (1958) 839) are already known as antituberculosis agents.

JP 53/28175 (78/28175) describes N,N'-bis(2-nitrooxyethyl)pyridine-2,4- and -2,5-dicarboxamides as substances having vasodilatory action.

Surprisingly, it has now been found that 2,4- and 2,5-substituted pyridine-N-oxides of the general formula I indicated below and the physiologically tolerable salts effectively inhibit lysine hydroxylase and proline hydroxylase in the animal model.

The invention accordingly relates to 2,4- and 2,5-substituted pyridine-N-oxides of the general formula I

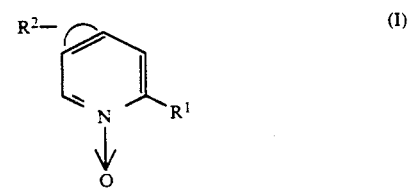

in which $R_1$ is —C(O)—X—$R^3$, where

X is O or —N($R^{3'}$)— and $R^3$ is hydrogen, $C_1$-$C_{12}$-alkyl, $C_2$-$C_{12}$-alkenyl, $C_2$-$C_{12}$-alkynyl, non-benzo-fused or benzo-fused or benzo-fused $C_5$-$C_7$-cycloalkyl, aryl or heteroaryl, where these radicals mentioned for $R^3$ are unsubstituted or are substituted by one or more identical or different radicals $R^4$, where $R^4$ is halogen, hydroxyl, cyano, nitro, nitroxy, amino, carboxyl, $C_1$-$C_4$-alkoxy, $C_1$-$C_4$-alkoxycarbonyl, $C_1$-$C_4$-alkyl- or -dialkylamino, indolyl or phenyl, where the indolyl or phenyl radical is unsubstituted or mono-substituted, disubstituted or trisubstituted by halogen, nitro, $C_1$-$C_4$-alkyl or $C_1$-$C_4$-alkoxy, where, in the case of polysubstitution, the radicals are identical or different or $R^3$, if X is —N($R^{3'}$), is a radical —N($R^5$)($R^6$), in which $R^5$ and $R^6$ are identical or different and are hydrogen, $C_1$-$C_4$-alkyl, $C_1$-$C_3$-alkylcarbonyl or phenyl and $R^{3'}$ has the meaning of $R^3$, where the radicals $R^3$ and $R^{3'}$ are identical or different or $R^3$ and $R^{3'}$, together with the nitrogen atom to which they are bonded, are a radical of the formula II

in which n is 1 to 3 and

A is O, S, $CH_2$ or —N($R^7$)—, where $R^7$ is hydrogen, phenyl, $C_1$-$C_6$-alkyl, $C_2$-$C_6$-alkenyl or $C_2$-$C_6$-alkynyl, where these mentioned radicals are unsubstituted or substituted by phenyl which, for its part, is unsubstituted, or monosubstituted or polysubstituted by one or more identical or different substituents selected from the group comprising: halogen, nitro, cyano, carboxyl, hydroxyl, methyl, ethyl, methoxy, ethoxy and trifluoromethyl or —$N(R^8)_2$, where $R^8$ is hydrogen or $C_1$–$C_3$-alkyl or

—$COOR^8$ or

—$CON(R^9)_2$ or $CONHR^7$, where $R^9$ has the meaning of $R^8$ or where $(R^9)_2$ is a $C_4$–$C_6$-alkylene chain in which no $CH_2$ group or a $CH_2$ group which is not directly adjacent to the nitrogen atom is replaced by O, S or N—$R^8$ or where $R^7$ is $C_1$–$C_4$-alkoxycarbonyl or $C_3$–$C_7$-cycloalkyl and in which $R^2$ has the meaning of $R^1$, where the radicals $R^1$ and $R^2$ are identical or different or $R^2$ is only present in the 4-position, and one of the radicals $R^3$ or $R^4$ is in the 5-position and the physiologically tolerable salts, where the compounds of the general formula I are excluded in which $R^1$ and $R^2$ are identical or different and are carboxyl, its methyl or ethyl esters and its diethylamides.

The invention furthermore relates to the use of compounds of the general formula I and the physiologically tolerable salts for the production of a pharmaceutical inhibiting proline hydroxylase and lysine hydroxylase.

Finally, the invention relates to the compounds of the general formula I for use as pharmaceuticals.

The invention relates in particular to the compounds of the formula I for use as fibrosuppressives and immunosuppressives and also for the inhibition of proline hydroxylase and lysine hydroxylase and for influencing the metabolism of collagen and collagen-like substances or the biosynthesis of Clq.

All said alkyl radicals having more than 2 carbon atoms can be either straight-chain or branched.

The invention furthermore relates to a process for the preparation of compounds of the general formula I.

The compounds according to the invention are most simply prepared by adding oxidants such as, for example, hydrogen peroxide or peracids such as peracetic acid, perfluoroacetic acid, perbenzoic acid or metachloroperbenzoic acid in solvents such as chlorinated hydrocarbons, such as, for example, methylene chloride, chloroform, tri- or tetrachloroethylene, benzene or toluene, to the pyridine compounds to be oxidized, which can likewise be dissolved in the abovementioned solvents, and stirring at a temperature between $-30°$ and $+40°$ C., preferably between $0°$ and $+25°$ C., for between 30 minutes and 3 days. Completion of the reaction can be determined, for example, by means of thin layer chromatography. The compounds according to the invention can preferably be prepared by employing the pyridine derivative and the oxidant in equimolar amounts or up to an about 5-fold excess of oxidant.

If appropriate, an excess of peracid can also be eliminated by introducing, for example, gaseous ammonia into the reaction solution and separating the resulting precipitate from the reaction solution by filtration.

If appropriate, the products can worked up, for example, by extraction or by chromatography, for example by means of silica gel. The isolated product can be recrystallized.

A general procedure for this oxidation method is also described, for example, in "E. Lingsberg, Pyridine and its Derivatives, Interscience Publishers, New York, 1961, Part 2, 93".

Oxidation with hydrogen peroxide is described, for example, in "E. Ochiai, J. Org. Chem. 18, 534 (1953)".

The preparation of the different pyridine derivatives necessary for the oxidation described is set out in the Patent Applications already cited as prior art. Those which may be mentioned are German Patent Applications P 38 26 471.4, 38 28 140.6, 39 24 093.2, 40 01 002.3 and DE-A-3,703,959, 3,703,962 and 3,703,963.

The compounds of the formula I according to the invention have useful pharmacological properties and in particular show activity as inhibitors of proline hydroxylase and lysine hydroxylase, as a fibrosuppressive, immunosuppressive and antiatherosclerotic The antifibrotic action can be determined in the carbon tetrachloride-induced liver fibrosis model. For this purpose, rats are treated twice weekly with $CCl_4$ (1 ml/kg) —dissolved in olive oil. The test substance is administered daily, if appropriate even twice daily, orally or intraperitoneally—dissolved in a suitable tolerable solvent. The extent of liver fibrosis is determined histologically and the proportion of collagen in the liver is analyzed by hydroxyproline determination—as described in Kivirikko et al. (Anal. Biochem. 19, 249 et seq. (1967)). The fibrogenesis activity can be determined by radioimmunological determination of collagen fragments and procollagen peptides in the serum. The compounds according to the invention are effective in this model in concentrations of 1–100 mg/kg.

The fibrogenesis activity can be determined by radioimmunological determination of the N-terminal propeptide of type III collagen or of the N- or C-terminal crosslinking domain of type IV collagen (7s collagen or type IV collagen-$NC_1$) in the serum.

For this purpose, the hydroxyproline, procollagen III peptide, 7s-collagen and type IV collagen-NC concentrations in the liver of a) untreated rats (control)

b) rats to which carbon tetrachloride was administered ($CCl_4$ control)

c) rats to which first CCl and then a compound according to the invention was administered were measured (this test method is described by Rouiller, C., experimental toxic injury of the liver; in The Liver, C. Rouiller, Vol. 2, pp. 335–476, New York, Academic Press, 1964).

Another model for the evaluation of antifibrotic action is bleomycin-induced lung fibrosis a described in Kelley et al. (J. Lab. Clin. Med. 96, 954, (1980)). The cotton pellet granuloma model, as described in Meier et al., Experientia 6, 469 (1950) can be used to evaluate the action of the compounds according to the invention in the granulation tissue.

The compounds of the formula I can be used as medicaments in the form of pharmaceutical preparations which contain them, if appropriate together with tolerable pharmaceutical carriers. The compounds can be used as medicaments, for example in the form of pharmaceutical preparations, which contain these compounds in a mixture with a pharmaceutical organic or inorganic carrier suitable for enteral, percutaneous or parenteral administration, such as, for example, water, gum arabic, gelatin, lactose, starch, magnesium stearate, talc, vegetable oils, polyalkylene glycols, petroleum jelly etc.

For this purpose, they can be administered orally in doses of 0.1-25 mg/kg/day, preferably 1-5 mg/kg/day or parenterally in doses of 0.01-5 mg/kg/day, preferably 0.01-2.5 mg/kg/day, in particular 0.5-1.0 mg/kg/day. In severe cases, the dosage can also be increased. In many cases, however, lower doses are also sufficient. This information relates to an adult weighing about 75 kg.

The invention furthermore includes the use of the compounds according to the invention in the production of pharmaceuticals which are employed for the treatment and prophylaxis of the abovementioned metabolic disorders.

The invention further relates to pharmaceuticals which contain one or more compounds of the formula I according to the invention and/or their physiologically tolerable salts.

The pharmaceuticals are prepared by processes which are known per se and which are familiar to the person skilled in the art. As pharmaceuticals, the pharmacologically active compounds according to the invention are employed either as such or preferably in combination with suitable pharmaceutical auxiliaries or excipients in the form of tablets, coated tablets, capsules, suppositories, emulsions, suspensions or solutions, the active compound content being up to about 95%, advantageously between 10 and 75%.

In addition to solvents, gel-forming agents, suppository bases, tablet auxiliaries and other active compound carriers, suitable auxiliaries or excipients for the desired pharmaceutical formulation are also, for example, antioxidants, dispersants, emulsifiers, antifoams, flavor correctants, preservatives, solubilizers or colorants.

The active compounds can be administered orally, parenterally or rectally.

The active compounds are mixed with the additives suitable for this purpose, such as excipients, stabilizers or inert diluents and brought into suitable administration forms, such as tablets, coated tablets, hard gelatin capsules, aqueous alcoholic or oily suspensions or aqueous or oily solutions, by the customary methods.

Inert excipients which can be used are, for example, gum arabic, magnesia, magnesium carbonate, potassium phosphate, lactose, glucose or starch, in particular corn starch. In this case, preparation can be carried out both as dry and as moist granules. Possible oily excipients or solvents are, for example, vegetable or animal oils, such as sunflower oil or cod liver oil.

For subcutaneous or intravenous administration, the active compounds are brought into solution, suspension or emulsion, if desired using the substances suitable for this such as solubilizers, emulsifiers or other auxiliaries. Suitable solvents are, for example, physiological saline solution or alcohols, for example ethanol, propanol or glycerol, and in addition also sugar solutions such as glucose or mannitol solutions, or, alternatively, a mixture of the various solvents mentioned.

The invention is illustrated in more detail below by Examples.

General procedure for the preparation of the compound 1 equivalent of pyridine derivative (for preparation see description) is initially introduced in methylene chloride and 1 equivalent of metachloroperbenzoic acid (MCPBA), dissolved in methylene chloride, is added dropwise at room temperature. The mixture is stirred at room temperature. After completion of the reaction, gaseous ammonia is blown into the solution with ice-cooling until a precipitate is no longer formed. The precipitate is filtered off, and the filtrate is dried with magnesium sulfate and concentrated.

The crude product is recrystallized or purified by means of thin layer chromatography.

The compounds mentioned in the following Examples are prepared according to this general procedure.

EXAMPLE 1

N,N'-Di-(2-methoxyethyl)pyridine-2,4-dicarboxamide N-oxide

From 1 g of N,N'-di-(2-methoxyethyl)pyridine-2,4-dicarboxamide and 0.62 g of MCPBA.

Yield: 620 mg (chromatography: ethyl acetate/methanol 5:1)

M.p.: 102° C.

EXAMPLE 2

N,N'-Di-(3-methoxypropyl)pyridine-2,4-dicarboxamide N-oxide

From 1 g of N,N'-di-(3-methoxypropyl)pyridine-2,4-dicarboxamide and 1.2 g of MCPBA.

Yield: 0.58 g (recrystallization: ethanol)

M.p.: 90° C.

EXAMPLE 3

Pyridine-2,4-dicarboxamide N-oxide

From 1 g of pyridine-2,4-dicarboxamide and 1.2 g of MCPBA.

Yield: 0.8 g (recrystallization: ethanol)

M.p.: 260° C.

EXAMPLE 4

N,N'-Di-(2-dimethoxyethyl)pyridine-2,4-dicarboxamide N-oxide

From 1 g of N,N'-di-(2-dimethoxyethyl)pyridine-2,4-dicarboxamide and 1.1 g of MCPBA.

Yield: 0.5 g (chromatography: ethyl acetate/methanol 5:1)

M.p.: 86° C.

EXAMPLE 5

N,N'-Di-(3-ethoxypropyl)pyridine-2,4-dicarboxamide N-oxide

From 1 g of N,N'-di-(3-ethoxypropyl)pyridine-2,4-dicarboxamide and 1.5 g of MCPBA.

Yield: 0.34 g (chromatography: ethyl acetate/methanol 5:1)

M.p.: 81° C.

EXAMPLE 6

N,N'-Di-(2-methoxyethyl)pyridine-2,5-dicarboxamide N-oxide

From 1 g of N,N'-di-(2-methoxyethyl)pyridine-2,4-dicarboxamide and 1.3 g of MCPBA.

Yield: 0.4 g (recrystallization: ethanol)

M.p.: 137° C.

EXAMPLE 7

Di-(2-methoxyethyl) pyridine-2,4-dicarboxylate N-oxide

From 1 g of di-(2-methoxyethyl) pyridine-2,4-dicarboxylate and 1.3 g of MCPBA.

Yield: 0.2 g (chromatography: ethyl acetate)

M.p.: oil

EXAMPLE 8

N,N'-Diethylpyridine-2,5-dicarboxamide N-oxide

From 1 g of N,N'-diethylpyridine-2,5-dicarboxamide and 1.8 g of MCPBA.
Yield: 0.4 g (recrystallization: ethanol)
M.p.: 128° C.

EXAMPLE 9

N,N'-Di-(3-methoxypropyl)pyridine-2,5-dicarboxamide N-oxide
From 1 g of N,N'-di-(3-methoxypropyl)pyridine-2,5-dicarboxamide and 1.2 g of MCPBA.
Yield: 0.3 g (recrystallization: diethyl ether/methanol)
M.p.: 123° C.

EXAMPLE 10

2,4-Di-[(morpholin-1-yl)carbonyl]pyridine N-oxide
From 1 g of 2,4-di-[(morpholin-1-yl)carbonyl]pyridine and 1,2 g of MCPBA.
Yield: 0.5 g (chromatography: ethyl acetate/methanol 5/1)
M.p.: oil

EXAMPLE 11

N,N'-Di-(4-hydroxybutyl)pyridine-2,4-dicarboxamide N-oxide
From 1 g of N,N'-di-(4-hydroxybutyl)pyridine-2,4-dicarboxamide and 0.8 g of MCPBA.
Yield: 0.82 g (ethanol)
M.p.: 88° C.

EXAMPLE 12

N,N'-Dicyclohexylpyridine-2,4-dicarboxamide N-oxide
From 1 g of N,N'-dicyclohexylpyridine-2,4-dicarboxamide and 0 g of MCPBA.
Yield: 0.59 g (ethanol)
M.p.: 153° C.

EXAMPLE 13

N,N'-Di-(3-chlorobenzyl)pyridine-2,4-dicarboxamide N-oxide
From 1 g of N,N'-di-(3-chlorobenzyl)pyridine-2,4-dicarboxamide and 0.65 g of MCPBA.
Yield: 0.76 g (toluene)
M.p.: 112° C.

EXAMPLE 14

N,N'-Di-(4-methylbenzyl)pyridine-2,4-dicarboxamide N-oxide
From 1 g of N,N'-di-(4-methylbenzyl)pyridine-2,4-dicarboxamide and 1.2 g of MCPBA.
Yield: 0.72 g (toluene)
M.p.: 153° C.

EXAMPLE 15

Di-(4-chlorobutyl) pyridine-2,4-dicarboxylate N-oxide
From 1 g of di-(4-chlorobutyl) pyridine-2,4-dicarboxylate and 0.75 g of MCPBA.
Yield: 0.83 g (ethanol)
M.p.: 98° C.

EXAMPLE 16

Dicyclohexyl pyridine-2,4-dicarboxylate N-oxide
From 1 g of dicyclohexyl pyridine-2,4-dicarboxylate and 0.75 g of MCPBA.
Yield: 0.87 g
Oil, MS =348 (M+H) molecular weight 347

EXAMPLE 17

Di-(methoxycarbonylmethyl) pyridine-2,4-dicarboxylate N-oxide
From 1 g of di-(methoxycarbonylmethyl) pyridine-2,4-dicarboxylate and 1.1 g of MCPBA.
Yield: 0.81 g
Oil, MS=328 (M+H) molecular weight 327

EXAMPLE 18

Pharmacological activity
In order to show the efficient inhibition of proline hydroxylase and lysine hydroxylase by the compounds according to the invention, the concentrations of bilirubin, bile acids and gamma GT in the serum of
a) untreated rats (control),
b) rats treated with CCl$_4$,
c) rats to which first CCl and then a compound according to the invention have been given,
are measured. (The method is described by Rouiller, C., Experimental toxic injury of the liver; in The Liver, C. Rouiller, Vol. 2, pages 335–476, New York, Academic Press 1964).
The results are summarized in Table 1.

TABLE 1

Action of prolyl hydroxylase inhibitors on CCl$_4$-induced liver fibrosis in rats

| Treatment | Dose[a] mg/kg | N | Bilirubin μm | Bile acids | Gamma GT U/L |
|---|---|---|---|---|---|
| Control | — | 5 | 1.76 ± 0.27 | 26 ± 6.8 | 2 ± 0 |
| CCl$_4$ | — | 22 | 4.98 ± 1.06 | 81 ± 8.7 | 5.3 ± 1.4 |
| Example 1 | 20 | 12 | 6.30 ± 5.4 (0) | 97 ± 76 (0) | 4.3 ± 3.1 (27) |
| Example 2 | 20 | 11 | 2.90 ± 0.94* (65) | 71 ± 42 (18) | 3.3 ± 2.2* (59) |

The results are mean values ± standard deviation.
*p < 0.05 for CCl$_4$ treatment.
values in brackets are the percentage improvement compared to an exclusive CCl$_4$ treatment.
[a]total daily oral dose.

We claim:
1. A 2,4- or 2,5-substituted pyridine-N-oxide of the formula I

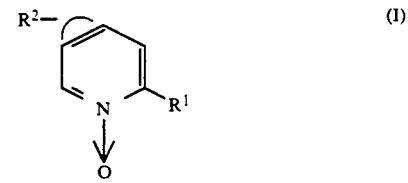

in which
$R^1$ is —C(O)—X—$R^3$, where
X is O or —N($R^{3'}$)— and
$R^3$ is hydrogen, $C_1$-$C_5$-alkyl, $C_6$-cycloalkyl, phenyl or pyridyl, where these radicals mentioned for $R^3$ are unsubstituted or are substituted by one or two identical radicals $R^4$, where
$R^4$ is hydroxyl, amino, carboxyl, $C_1$—$C_4$-alkoxy, $C_1$-$C_4$-alkoxycarbonyl or phenyl, where the phenyl radical is unsubstituted or monosubstituted by methyl or methoxy
and
$R^{3'}$ has the meaning of $R^3$, where the radicals $R^3$ and $R^{3'}$ are identical or different or
$R^3$ and $R^{3'}$, together with the nitrogen atom to which they are bonded, are a radical of the formula II

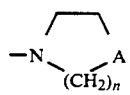

in which n is 2 and

A is $CH_2$, and in which $R^2$ has the meaning of $R^1$, where the radicals $R^1$ and $R^2$ are identical or different or $R^2$ is only present in the 4-position, and one of the radicals $R^3$ or $R^4$ is in the 5-position or a physiologically tolerable salt thereof, excluding compounds of the general formula I in which $R^1$ and $R^2$ are identical or different and are carboxyl, its methyl or ethyl esters and its diethylamides, and excluding 2-pyridine carboxylic acid-5-(octylaminocarbonyl)-1-oxide.

2. A pharmaceutical composition comprising a pharmaceutically tolerable carrier and an effective amount of a 2,4- or 2,5-substituted pyridine-N-oxide of the formula I

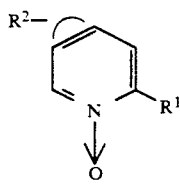

in which $R^1$ is $—C(O)—X—R^3$, where

X is O or $—N(R^{3'})—$ and $R^3$ is hydrogen, $C_1-C_{12}$-alkyl, $C_2-C_{12}$-alkenyl, $C_2-C_{12}$-alkynyl, non-benzo-fused or benzo-fused $C_5-C_7$-cycloalkyl, aryl or pyridyl where these radicals mentioned for $R^3$ are unsubstituted or are substituted by one or more identical or different radicals $R^4$, where $R^4$ is halogen, hydroxyl, cyano, nitro, nitroxy, amino, carboxyl, $C_1-C_4$-alkoxy, $C_1-C_4$-alkoxycarbonyl, $C_1-C_4$-alkyl- or -dialkylamino, phenyl, where the phenyl radical is unsubstituted or monosubstituted, disubstituted or trisubstituted by halogen, nitro, $C_1—C_4$-alkyl or $C_1-C_4$-alkoxy, wherein, in the case of polysubstitution, the radicals are identical or different or $R^3$, if X is $—N(R^{3'})$, is a radical $—N(R^5)(R^6)$, in which $R^5$ and $R^6$ are identical or different and are hydrogen, $C_1-C_4$-alkyl, $C_1-C_3$-alkylcarbonyl or phenyl and $R^{3'}$ has the meaning of $R^3$, where the radicals $R^3$ and $R^{3'}$ are identical or different or $R^3$ and $R^{3'}$, together with the nitrogen atom to which they are bonded, are a radical of the formula II

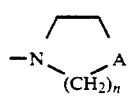

in which n is 2 and

A is $CH_2$ and in which $R^2$ has the meaning of $R^1$, where the radicals $R^1$ and $R^2$ are identical or different or $R^2$ is only present in the 4-position, and one of the radicals $R^3$ or $R^4$ is in the 5-position or a physiologically tolerable salt thereof.

3. A pharmaceutical composition comprising a pharmaceutically tolerable carrier and an effective amount of a compound as claimed in claim 1 or a physiologically tolerable salt thereof.

4. A method of inhibiting proline hydroxylase and lysine hydroxylase which comprises applying to a subject an effective amount of a 2,4- or 2,5-substituted pyridine-N-oxide of the formula I

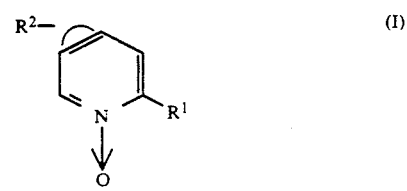

in which $R^1$ is $—C(O)—X—R^3$, where

X is O or $—N(R^{3'})—$ and $R^3$ is hydrogen, $C_1-C_6$-alkyl, $C_2-C_6$-alkenyl, $C_2-C_6$-alkynyl, $C_5-C_7$-cycloalkyl, aryl pyridyl, where these radicals mentioned for $R^3$ are unsubstituted or are substituted by one or two identical or different radicals $R^4$, where $R^4$ is halogen, hydroxyl, cyano, amino, carboxyl, $C_1-C_4$-alkoxy, $C_1-C_4$-alkoxycarbonyl, $C_1-C_4$-alkyl- or -dialkylamino, or phenyl, where the phenyl radical is unsubstituted or monosubstituted by halogen, $C_1-C_2$-alkyl or $C_1-C_2$-alkoxy and $R^{3'}$ has the meaning of $R^3$, where the radicals $R^3$ and $R^{3'}$ are identical or different or $R^3$ and $R^{3'}$, together with the nitrogen atom to which they are bonded, are a radical of the formula II

in which n is 2 and

A is $CH_2$ and in which $R^2$ has the meaning of $R^1$, where the radicals $R^1$ and $R^2$ are identical or different or $R^2$ is only present in the 4-position, and one of the radicals $R^3$ or $R^4$ is in the 5-position or a physiologically tolerable salt thereof.

5. A method of treating a subject in need of a fibrosuppressive or immunosuppressive which comprises administering an effective amount of a 2,4- or 2,5-substituted pyridine-N-oxide of the formula I

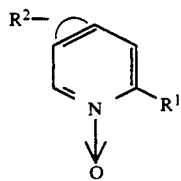

in which
R$^1$ is —C(O)—X—R$^3$, where
X is O or —N(R$^{3'}$)— and
R$^3$ is hydrogen, C$_1$-C$_5$-alkyl, C$_6$-cycloalkyl, phenyl or pyridyl, where these radicals mentioned for R$^3$ are unsubstituted or are substituted by one or two identical radicals R$^4$, where
R$^4$ is hydroxyl, amino, carboxyl, C$_1$-C$_4$-alkoxy, C$_1$-C$_4$-alkoxycarbonyl or phenyl, where the phenyl radical is unsubstituted or monosubstituted by methyl or methoxy
and
R$^{3'}$ has the meaning of R$^3$, where the radicals R$^3$ and R$^{3'}$ are identical or different or
R$^3$ and R$^{3'}$, together with the nitrogen atom to which they are bonded, are a radical of the formula II

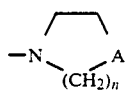

in which
n is 2 and
A is CH$_2$,
and in which
R$^2$ has the meaning of R$^1$, where the radicals R$^1$ and R$^2$ are identical or different
or R$^2$ is only present in the 4-position, and one of the radicals R$^3$ or R$^4$ is in the 5-position
or a physiologically tolerable salt thereof.

6. A method of influencing the metabolism of collagen and collagen-like substances or the biosynthesis of Clq which comprises applying to a subject an effective amount of a 2,4- or 2,5-substituted pyridine-N-oxide of the formula I

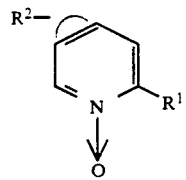

in which
R$^1$ is —C(O)—X—R$^3$, where
X is O or —N(R$^{3'}$)— and
R$^3$ is hydrogen, C$_1$-C$_{12}$-alkyl, C$_2$-C$_{12}$-alkenyl, C$_2$-C$_{14}$-alkynyl, non-benzo-fused or benzo-fused C$_5$-C$_7$-cycloalkyl, aryl or pyridyl, where these radicals mentioned for R$^3$ are unsubstituted or are substituted by one or more identical or different radicals R$^4$, where
R$^4$ is halogen, hydroxyl, cyano, nitro, nitroxy, amino, carboxyl, C$_1$-C$_4$-alkoxy, C$_1$-C$_4$-alkoxycarbonyl, C$_1$-C$_4$-alkyl- or -dialkylamino, phenyl, where the phenyl radical is unsubstituted or monosubstituted, disubstituted or trisubstituted by halogen, nitro, C$_1$-C$_4$-alkyl or C$_1$-C$_4$-alkoxy, where, in the case of polysubstitution, the radicals are identical or different
or
R$^3$, if X is —N(R$^{3'}$), is a radical —N(R$^5$)(R$^6$), in which
R$^5$ and R$^6$ are identical or different and are hydrogen, C$_1$-C$_4$-alkyl, C$_1$-C$_3$-alkylcarbonyl or phenyl
and
R$^{3'}$ has the meaning of R$^3$, where the radicals R$^3$ and R$^{3'}$ are identical or different or
R$^3$ and R$^{3'}$, together with the nitrogen atom to which they are bonded, are a radical of the formula II

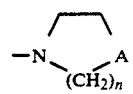

in which
n is 2 and
A is CH$_2$
R$^2$ has the meaning of R$^1$, where the radicals R$^1$ and R$^2$ are identical or different
or R$^2$ is only present in the 4-position, and one of the radicals R$^3$ or R$^4$ is in the 5-position
or a physiologically tolerable salt thereof.

7. A method of treating disorders of the metabolism of collagen and collagen-like substances or the biosynthesis of Clq which comprises applying to a subject an effective amount of a 2,4- or 2,5-substituted pyridine-N-oxide of the formula I

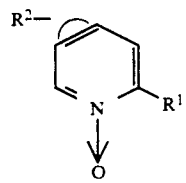

in which
R$^1$ is —C(O)—X—R$^3$, where
X is O or —N(R$^{3'}$)— and
R$^3$ is hydrogen, C$_1$-C$_{12}$-alkyl, C$_2$-C$_{12}$-alkenyl, C$_2$-C$_{12}$-alkynyl, non-benzo-fused or benzo-fused C$_5$-C$_7$-cycloalkyl, aryl or pyridyl, where these radicals mentioned for R$^3$ are unsubstituted or are substituted by one or more identical or different radicals R$^4$, where
R$^4$ is halogen, hydroxyl, cyano, nitro, nitroxy, amino, carboxyl, C$_1$-C$_4$-alkoxy, C$_1$-C$_4$-alkoxycarbonyl, C$_1$-C$_4$-alkyl- or -dialkylamino, phenyl, where the phenyl radical is unsubstituted or monosubstituted, disubstituted or trisubstituted by halogen, nitro, C$_1$-C$_4$-alkyl or C$_1$-C$_4$-alkoxy, where, in the case of polysubstitution, the radicals are identical or different
or
R$^3$, if X is —N(R$^{3'}$), is a radical —N(R$^5$)(R$^6$), in which
R$^5$ and R$^6$ are identical or different and are hydrogen, C$_1$-C$_4$-alkyl, C$_1$-C$_3$-alkylcarbonyl or phenyl
and
R$^{3'}$ has the meaning of R$^3$, where the radicals R$^3$ and R$^{3'}$ are identical or different or $R^3$ and $R^{3'}$, together with the nitrogen atom to which they are bonded, are a radical of the formula II

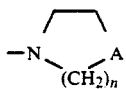
(II)

in which
n is 2 and
A is $CH_2$
and in which
$R^2$ has the meaning of $R^1$, where the radicals $R^1$ and $R^2$ are identical or different
or $R^2$ is only present in the 4-position, and one of the radicals $R^3$ or $R^4$ is in the 5-position
or a physiologically tolerable salt thereof.

8. A method of inhibiting proline hydroxylase and lysine hydroxylase which comprises applying to a subject an effective amount of a compound as claimed in claim 1 or a physiologically tolerable salt thereof.

9. A method of treating a subject in need of a fibrosuppressive or immunosuppressive which comprises administering an effective amount of a compound as claimed in claim 1 or a physiologically tolerable salt thereof.

10. A method of influencing the metabolism of collagen and collagen-like substances or the biosynthesis of Clq which comprises applying to a subject an effective amount of a compound as claimed in claim 1 or a physiologically tolerable salt thereof.

11. A method of treating disorders of the metabolism of collagen and collagen-like substances or the biosynthesis of Clq which comprises applying to a subject an effective amount of the compound as claimed in claim 1 or a physiologically tolerable salt thereof.

* * * * *